United States Patent
Onishi

(10) Patent No.: US 9,409,207 B2
(45) Date of Patent: Aug. 9, 2016

(54) ULTRASONIC DEVICE, ULTRASONIC PROBE, ELECTRONIC EQUIPMENT, AND ULTRASONIC IMAGING APPARATUS

(71) Applicant: SEIKO EPSON CORPORATION, Tokyo (JP)

(72) Inventor: Yasunori Onishi, Nagano (JP)

(73) Assignee: Seiko Epson Corporation, Tokyo (JP)

( * ) Notice: Subject to any disclaimer, the term of this patent is extended or adjusted under 35 U.S.C. 154(b) by 376 days.

(21) Appl. No.: 14/164,680

(22) Filed: Jan. 27, 2014

(65) Prior Publication Data

US 2014/0208853 A1 Jul. 31, 2014

(30) Foreign Application Priority Data

Jan. 28, 2013 (JP) ................................. 2013-012946

(51) Int. Cl.
| | |
|---|---|
| *B06B 3/04* | (2006.01) |
| *B06B 1/06* | (2006.01) |
| *G01N 29/06* | (2006.01) |
| *B06B 3/00* | (2006.01) |
| *G10K 11/30* | (2006.01) |

(52) U.S. Cl.
CPC ................. *B06B 1/0622* (2013.01); *B06B 3/00* (2013.01); *G10K 11/30* (2013.01); *G01N 29/0654* (2013.01)

(58) Field of Classification Search
CPC .... B06B 1/0622; B06B 3/00; G01N 29/0654; G10K 11/30
USPC ..................... 73/606; 310/319, 335
See application file for complete search history.

(56) References Cited

U.S. PATENT DOCUMENTS

| | | | |
|---|---|---|---|
| 4,957,100 A | 9/1990 | Herzog et al. | |
| 5,050,128 A * | 9/1991 | Saitoh ..................... | G10K 11/02 310/335 |
| 5,423,220 A * | 6/1995 | Finsterwald .......... | B06B 1/0622 310/322 |
| 6,418,084 B2 * | 7/2002 | Saito ...................... | G10K 11/30 367/150 |
| 2002/0105250 A1 | 8/2002 | Klee et al. | |
| 2014/0211587 A1* | 7/2014 | Kiyose ................ | G01S 7/52053 367/7 |
| 2015/0216504 A1* | 8/2015 | Kiyose ................ | B06B 1/06259 600/472 |

FOREIGN PATENT DOCUMENTS

| | | | |
|---|---|---|---|
| JP | 63-252583 A | 10/1988 | |
| JP | 03-143433 A | 6/1991 | |
| JP | 2002-271897 A | 9/2002 | |
| JP | 2007-201901 A | 8/2007 | |
| JP | 2009-072370 A | 4/2009 | |

* cited by examiner

*Primary Examiner* — J M Saint Surin
(74) *Attorney, Agent, or Firm* — Global IP Counselors, LLP

(57) ABSTRACT

Provided is an ultrasonic device including: an ultrasonic element array substrate having a plurality of ultrasonic elements that each include a piezoelectric body; an acoustic lens secured via an acoustic matching layer to a surface, formed with the ultrasonic elements, of the ultrasonic element array substrate; and a support member secured to a surface, opposite to the surface formed with the ultrasonic elements, of the ultrasonic element array substrate, wherein the support member is formed to have a larger area, in plan view in the thickness direction of the ultrasonic element array substrate, and a higher bending stiffness than the ultrasonic element array substrate, and the acoustic lens is formed to have a lower bending stiffness than the ultrasonic element array substrate. The above-described ultrasonic device further includes an acoustic matching layer filled between the ultrasonic element array substrate and the acoustic lens.

20 Claims, 10 Drawing Sheets

ULTRASONIC DEVICE, ULTRASONIC PROBE, ELECTRONIC EQUIPMENT, AND ULTRASONIC IMAGING APPARATUS

BACKGROUND

1. Technical Field

The present invention relates to an ultrasonic device, an ultrasonic probe, electronic equipment, and an ultrasonic imaging apparatus.

2. Related Art

Up to the present time, ultrasonic elements that transmit and receive ultrasound have been known. For example, JP-A-2002-271897, which is an example of related art, discloses ultrasonic elements (ultrasonic transducers) each having a structure in which a substrate is provided with an opening, and a film, a first electrode, a piezoelectric layer, and a second electrode are sequentially layered over the opening. As the substrate of the ultrasonic elements, silicon substrates or the like are used. On such a silicon substrate, the first and second electrodes and the piezoelectric layer formed of thin films are provided.

The structure of the ultrasonic elements disclosed in JP-A-2002-271897 is susceptible to damage by external forces, because of an opening provided in the substrate that is made of a brittle material.

In particular, such a structure suffers from a problem that, if an impact force is externally applied to an acoustic lens by being dropped or the like, the ultrasonic elements or the substrates of the ultrasonic elements are susceptible to damage.

SUMMARY

Some aspects of the invention can be realized in the form of the following embodiments or application examples.

Application Example 1

An ultrasonic device according to this application example includes: an ultrasonic element array substrate having a plurality of ultrasonic elements that each include a piezoelectric body and perform at least one of transmission and reception of ultrasound; an acoustic lens secured via an acoustic matching layer to a surface, formed with the ultrasonic elements, of the ultrasonic element array substrate, the acoustic lens having a lens portion that focuses the ultrasound; and a support member secured to a surface, opposite to the surface formed with the ultrasonic elements, of the ultrasonic element array substrate. The support member is formed to have a larger area, in plan view in the thickness direction of the ultrasonic element array substrate, and a higher bending stiffness than the ultrasonic element array substrate. The acoustic lens is formed to have a lower bending stiffness than the ultrasonic element array substrate.

According to this configuration, the ultrasonic element array substrate has one surface to which the support member is secured and another surface to which the acoustic lens is secured. Further, the support member is formed to have a larger area and a higher bending stiffness than the ultrasonic element array substrate, and the acoustic lens is formed to have a lower bending stiffness than the ultrasonic element array substrate.

In this way, the ultrasonic element array substrate has a structure in which it is secured to the support member having a higher bending stiffness than the ultrasonic element array substrate, and thereby the ultrasonic element array substrate is reinforced and is made difficult to warp.

Furthermore, the acoustic matching layer is provided between the ultrasonic element array substrate and the acoustic lens. Therefore, the acoustic lens having a lower bending stiffness and the acoustic matching layer absorb external forces applied to the ultrasonic element array substrate so that the external forces are relaxed. Thus, it is possible to suppress damage to the ultrasonic element array substrate.

Application Example 2

It is preferable that the ultrasonic device according to the above-mentioned application example further includes an acoustic matching layer provided between the ultrasonic element array substrate and the acoustic lens, and the acoustic matching layer be formed of a resin secured to the ultrasonic element array substrate and the acoustic lens.

According to this configuration, the acoustic matching layer is composed of a resin, and the ultrasonic element array substrate and the acoustic lens can be bonded to each other with an adhesive.

Therefore, the cured adhesive (resin) serves to bond the ultrasonic element array substrate and the acoustic lens to each other, and has a function also as an acoustic matching layer.

Application Example 3

In the ultrasonic device according to the above-mentioned application example, the acoustic lens preferably has a plurality of first projections in contact with the ultrasonic element array substrate.

According to this configuration, the acoustic lens has the first projections that specify the distance between the ultrasonic element array substrate and the lens portion of the acoustic lens.

Therefore, setting the length of the first projections allows the distance between the surface of the ultrasonic element array substrate and the lens portion to be easily set, thereby specifying the thickness of the acoustic matching layer arranged between the ultrasonic element array substrate and the lens portion.

Application Example 4

In the ultrasonic device according to the above-mentioned application example, the first projections are preferably provided in a peripheral portion of the acoustic lens in the plan view.

According to this configuration, the first projections are provided in the peripheral portion of the acoustic lens.

In this way, the acoustic lens can be stably mounted on the ultrasonic element array substrate, which allows the distance between the surface of the ultrasonic element array substrate and the lens portion to be set accurately.

Application Example 5

It is preferable that the ultrasonic device according to the above-mentioned application example further includes a flexible printed circuit board connected to the surface, formed with the ultrasonic elements, of the ultrasonic element array substrate, the flexible printed circuit board be electrically connected to the ultrasonic element array substrate, and a part of the flexible printed circuit board be secured to the support member.

According to this configuration, a flexible printed circuit board is provided that is connected to the ultrasonic element array substrate on the side to which the acoustic lens is secured, and a part of the flexible printed circuit board is secured to the support member.

Since a part of the flexible printed circuit board is secured to the support member, tension applied to the flexible printed circuit board does not act on the portion connected to the ultrasonic element array substrate, so that separation of the connected portion and damage to the ultrasonic element array substrate can be prevented.

Application Example 6

In the ultrasonic device according to the above-mentioned application example, it is preferable that the support member includes an angled portion provided at a part of its outer edge, and the flexible printed circuit board be secured to the angled portion.

According to this configuration, the angled portion is provided at a part of the outer edge of the support member, and the flexible printed circuit board is secured to the angled portion. Therefore, the flexible printed circuit board extends along the angled portion without being folded.

Therefore, it is possible to prevent line disconnection of the flexible printed circuit board, so as to provide an ultrasonic device with high reliability.

Application Example 7

In the ultrasonic device according to the above-mentioned application example, it is preferable that the acoustic lens have a plurality of second projections, in contact with the flexible printed circuit board, pressing the flexible printed circuit board against the ultrasonic element array substrate.

According to this configuration, the second projections of the acoustic lens are in contact with the flexible printed circuit board. Therefore, it is possible to prevent the flexible printed circuit board from being lifted in the connected portion between the ultrasonic element array substrate and the flexible printed circuit board by the second projections pressing the flexible printed circuit board.

Application Example 8

In the ultrasonic device according to the above-mentioned application example, it is preferable that the flexible printed circuit board is electrically connected with the ultrasonic element array substrate at a position between the second projections of the acoustic lens and the ultrasonic elements, in plan view in the thickness direction of the ultrasonic element array substrate.

According to this configuration, since the flexible printed circuit board is connected with the ultrasonic element array substrate at a position inside the periphery of the acoustic lens, the connected portion is not exposed. Further, the connected portion can be protected by the acoustic matching layer.

Application Example 9

In the ultrasonic device according to the above-mentioned application example, it is preferable that the ultrasonic element array substrate includes: a base substrate provided with a plurality of openings arranged in an array; a vibrating membrane formed to cover the openings, the vibrating membrane being displaceable in a film thickness direction; and a piezoelectric body provided on the vibrating membrane. It is also preferable that the piezoelectric body includes a first electrode provided on the vibrating membrane; a piezoelectric layer provided to cover at least part of the first electrode; and a second electrode provided to cover at least part of the piezoelectric layer.

According to this configuration, the ultrasonic element array substrate includes the base substrate provided with the plurality of openings arranged in an array; the vibrating membrane formed to cover the openings, the vibrating membrane being displaceable in the film thickness direction; and the piezoelectric body provided on the vibrating membrane, the piezoelectric body being formed by layering the first electrode, the piezoelectric layer, and the second electrode on the vibrating membrane.

In the ultrasonic device having such a configuration, the ultrasonic element array substrate can be downsized, leading to a reduction in size of the ultrasonic device.

Application Example 10

An ultrasonic probe according to this application example includes: the ultrasonic device described above; and a housing supporting the ultrasonic device.

According to this configuration, the ultrasonic device described above and the housing supporting the ultrasonic device are provided.

The ultrasonic probe of this application example includes, in the housing, the ultrasonic device that prevents damage to the ultrasonic element array substrate. Thus, it is possible to provide an ultrasonic probe with high reliability.

Application Example 11

Electronic equipment according to this application example includes: the ultrasonic device described above; and a processing circuit that is connected to the ultrasonic device and processes an output of the ultrasonic device.

According to this configuration, the ultrasonic device described above and the processing circuit that processes the output of the ultrasonic device are provided.

The electronic equipment of this application example includes the ultrasonic device that prevents damage to the ultrasonic element array substrate. Thus, it is possible to provide electronic equipment with high reliability.

Application Example 12

An ultrasonic imaging apparatus according to this application example includes: the ultrasonic device described above; a processing circuit that is connected to the ultrasonic device and processes an output of the ultrasonic device so as to generate an image; and a display that displays the image.

According to this configuration, the ultrasonic device described above, the processing circuit that processes an output of the ultrasonic device so as to generate an image, and the display that displays the image are provided.

The ultrasonic imaging apparatus of this application example includes the ultrasonic device that prevents damage to the ultrasonic element array substrate. Thus, it is possible to provide an ultrasonic imaging apparatus with high reliability.

BRIEF DESCRIPTION OF THE DRAWINGS

The invention will be described with reference to the accompanying drawings, wherein like numbers reference like elements.

DESCRIPTION OF EXEMPLARY EMBODIMENTS

Figure 1:
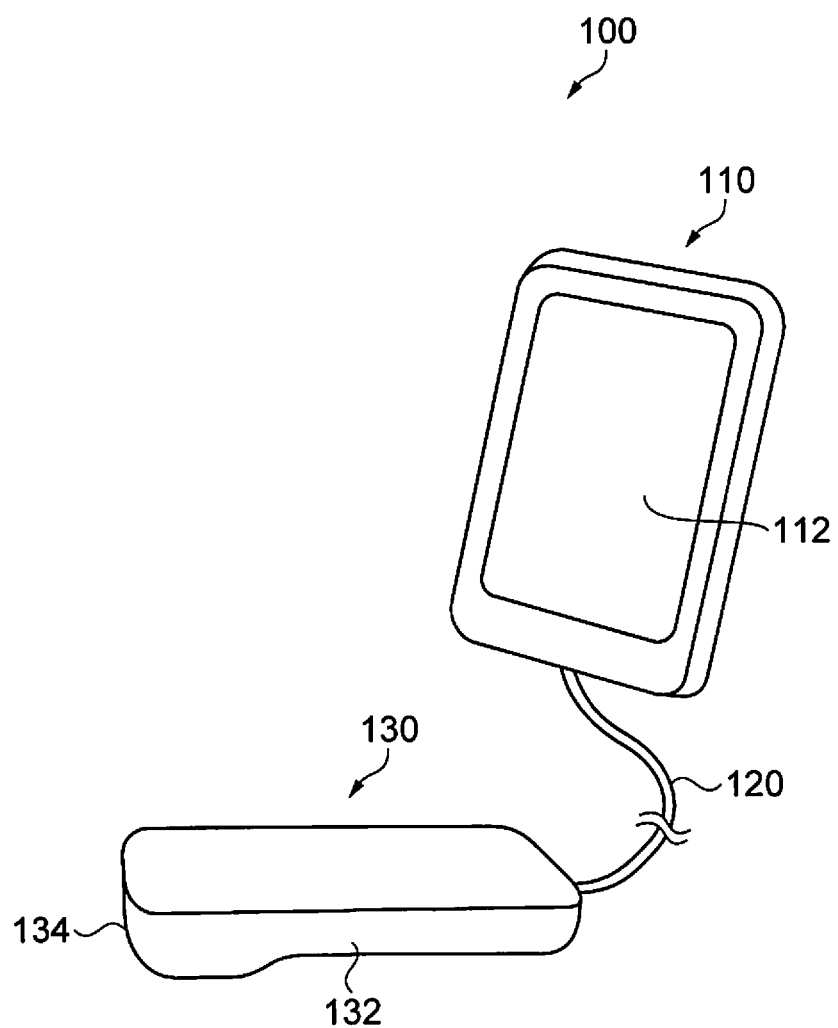
FIG. 1 is a schematic outline showing a configuration of an ultrasonic imaging apparatus of a first embodiment.

Hereinafter, embodiments for implementing the invention are described with reference to the drawings. It should be noted that, in the drawings herein referred to for the following descriptions, the dimensional ratio of each component is appropriately changed so that the component is scaled to a recognizable size.

First Embodiment

In this embodiment, an ultrasonic imaging apparatus for inspecting the inside of the human body is described as an example of electronic equipment.

(1) Overall Configuration of Ultrasonic Imaging Apparatus

Figure 2:
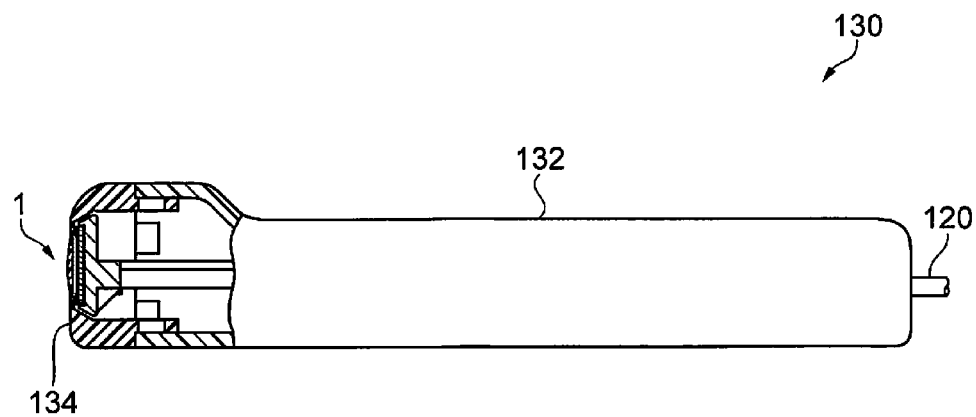
FIG. 2 is a partial sectional view of an ultrasonic probe according to the first embodiment.
Figure 3:
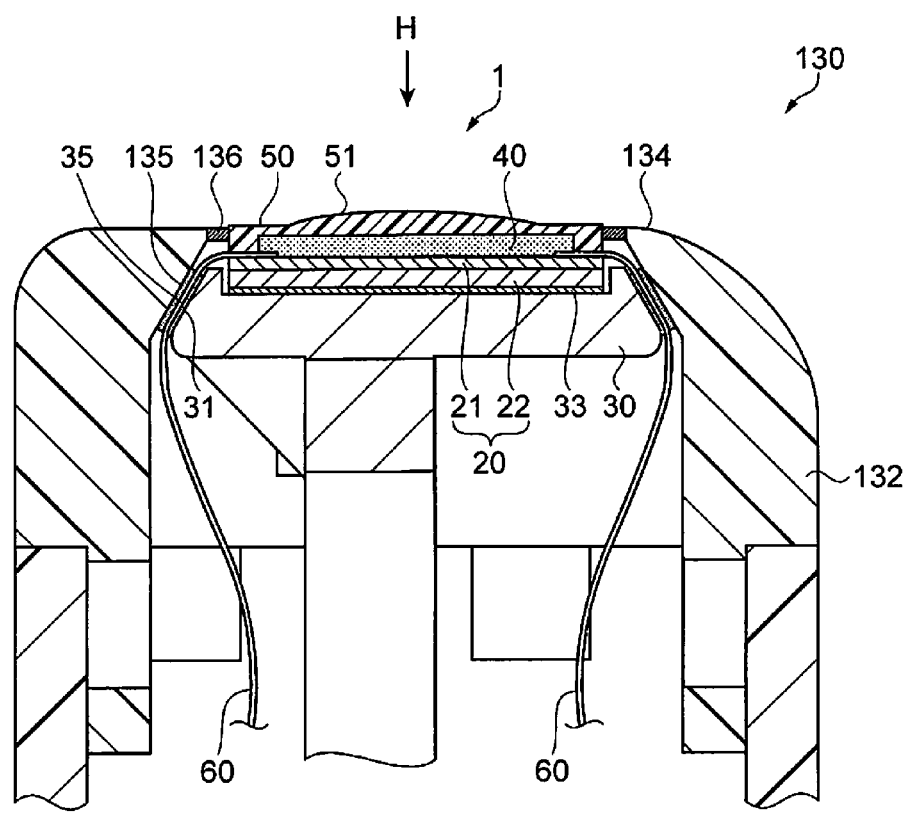
FIG. 3 is an enlarged sectional view of a head portion of the ultrasonic probe according to the first embodiment.

FIG. 1 shows a schematic outline of an ultrasonic imaging apparatus of this embodiment. FIG. 2 is a partial sectional view of an ultrasonic probe. FIG. 3 is an enlarged sectional view of a head portion of the ultrasonic probe.

As shown in FIG. 1, an ultrasonic imaging apparatus 100 includes an apparatus body 110 and an ultrasonic probe 130. The apparatus body 110 and the ultrasonic probe 130 are connected to each other by a cable 120. The apparatus body 110 and the ultrasonic probe 130 can exchange electrical signals via the cable 120.

The apparatus body 110 incorporates a display panel or the like as a display 112. In this embodiment, the display 112 is a touch panel display, and serves also as a user-interface unit (UI unit).

In the apparatus body 110, images are produced on the basis of ultrasound detected by the ultrasonic probe 130, and the thus produced images of the detection results are displayed on the screen of the display 112.

The ultrasonic probe 130 includes a housing 132 having a rectangular parallelepiped shape. The cable 120 is connected to one end in the longitudinal direction of the housing 132. On the opposite side, a head portion 134 that transmits and receives ultrasound is provided.

The ultrasonic imaging apparatus 100 of this embodiment is realized so that the apparatus body 110 and the ultrasonic probe 130 are connected by the cable 120. However, it may be realized so that the apparatus body 110 and the ultrasonic probe 130 wirelessly exchange signals without using the cable 120.

As shown in FIG. 2 and FIG. 3, the ultrasonic probe 130 includes an ultrasonic device 1 accommodated within the housing 132. The surface of the ultrasonic device 1 is exposed on the surface of the head portion 134 of the housing 132, so that ultrasound can be output from the surface of the head portion 134 toward a target object, and reflected waves of the ultrasound (echo waves) can be received from the object.

As shown in FIG. 3, there is a gap between the ultrasonic device 1 and the head portion 134 of the housing 132. A sealing portion 136 filled with a silicone-based sealing material is provided in the gap. This sealing portion 136 prevents water, etc., from entering the ultrasonic device 1 in the housing 132 of the ultrasonic probe 130.

Further, there is also provided a sealing structure for forming a seal with a support member 30 of the ultrasonic device 1, which will be mentioned later. This sealing structure maintains pressure contact between an adhesive member 35, such as double-sided adhesive tape, which has elasticity and is attached to the peripheral portion of the support member 30 of the ultrasonic device 1, and an adhesive member 135, such as double-sided adhesive tape, which has elasticity and is attached to the housing 132.

Further, a flexible printed circuit board (hereinafter, which may be referred to also as an FPC (Flexible Printed Circuit)) 60 for connection between the ultrasonic device 1 and a processing circuit is interposed in a part of this sealing portion. In this part, the adhesive members 35 and 135 are pressed against each other with the FPC 60 being interposed therebetween.

It should be noted that a double-sided adhesive tape formed of a closed cell material, such as polyethylene and urethane, coated with an acrylic adhesive is used as the adhesive members 35 and 135.

As described above, the ultrasonic probe 130 of this embodiment employs a double sealing structure, thereby preventing water, etc., from entering the housing 132.

Figure 4:
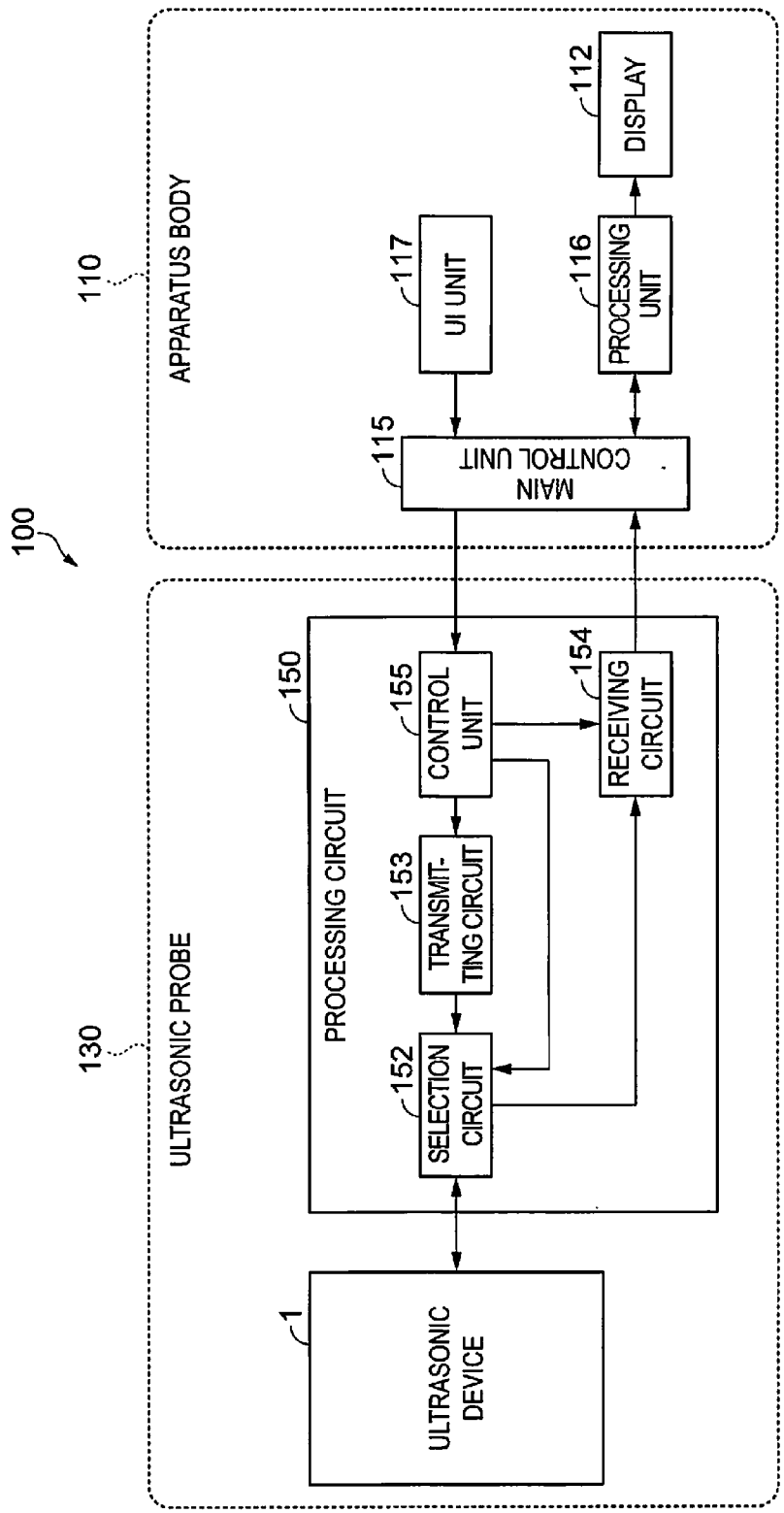
FIG. 4 is a control block diagram of an ultrasonic imaging apparatus according to the first embodiment.

FIG. 4 is a control block diagram of the ultrasonic imaging apparatus 100.

The ultrasonic imaging apparatus 100 includes the apparatus body 110 and the ultrasonic probe 130 as mentioned above.

The ultrasonic probe 130 includes the ultrasonic device 1 and a processing circuit 150.

The processing circuit 150 has a selection circuit 152, a transmitting circuit 153, a receiving circuit 154, and a control unit 155. This processing circuit 150 performs transmission processing and reception processing for the ultrasonic device 1.

The transmitting circuit 153 outputs transmission signals VT to the ultrasonic device 1 via the selection circuit 152 in a transmission period. Specifically, the transmitting circuit 153 generates the transmission signals VT, on the basis of control by the control unit 155, and outputs them to the selection circuit 152. Then, the selection circuit 152 outputs the transmission signals VT from the transmitting circuit 153, on the basis of control by the control unit 155. The frequency and amplitude voltage of the transmission signals VT can be set by the control unit 155.

The receiving circuit 154 performs reception processing on reception signals VR from the ultrasonic device 1. Specifically, the receiving circuit 154 receives the reception signals VR from the ultrasonic device 1 via the selection circuit 152 in a reception period, and performs reception processing such as amplification of the reception signals, gain setting, frequency setting, and A/D conversion (analog/digital conversion). The results of reception processing are output as detected data (detected information) to a processing unit 116 of the apparatus body 110. The receiving circuit 154, for example, can be composed of a low-noise amplifier, a voltage-controlled attenuator, a programmable gain amplifier, a low-pass filter, an A/D converter, and the like.

The control unit 155 controls the transmitting circuit 153 and the receiving circuit 154. Specifically, the control unit 155 controls the transmitting circuit 153 for generation of the transmission signals VT and the output processing, and controls the receiving circuit 154 for frequency setting of the reception signals VR, gain, or the like.

The selection circuit 152 outputs the selected transmission signals VT on the basis of control by the control unit 155.

The apparatus body 110 includes the display 112, a main control unit 115, the processing unit 116, and a UI unit (user-interface unit) 117.

The main control unit 115 controls the ultrasonic probe 130 for transmission and reception of ultrasound, and controls the processing unit 116 for image processing of detected data, or the like.

The processing unit 116 receives detected data from the receiving circuit 154, and performs necessary image processing, generation of image data to be displayed, or the like.

The UI unit 117 outputs necessary instruction (command) to the main control unit 115 on the basis of user operation (e.g., touch panel operation).

The display 112, for example, is a liquid crystal display, and displays the image data to be displayed from the processing unit 116.

It should be noted that part of control by the main control unit 115 may be performed by the control unit 155 of the processing circuit 150, or part of control by the control unit 155 may be performed by the main control unit 115.

(2) Configuration of Ultrasonic Device

Next, a configuration of the ultrasonic device incorporated in the ultrasonic probe is described.

Figure 5:
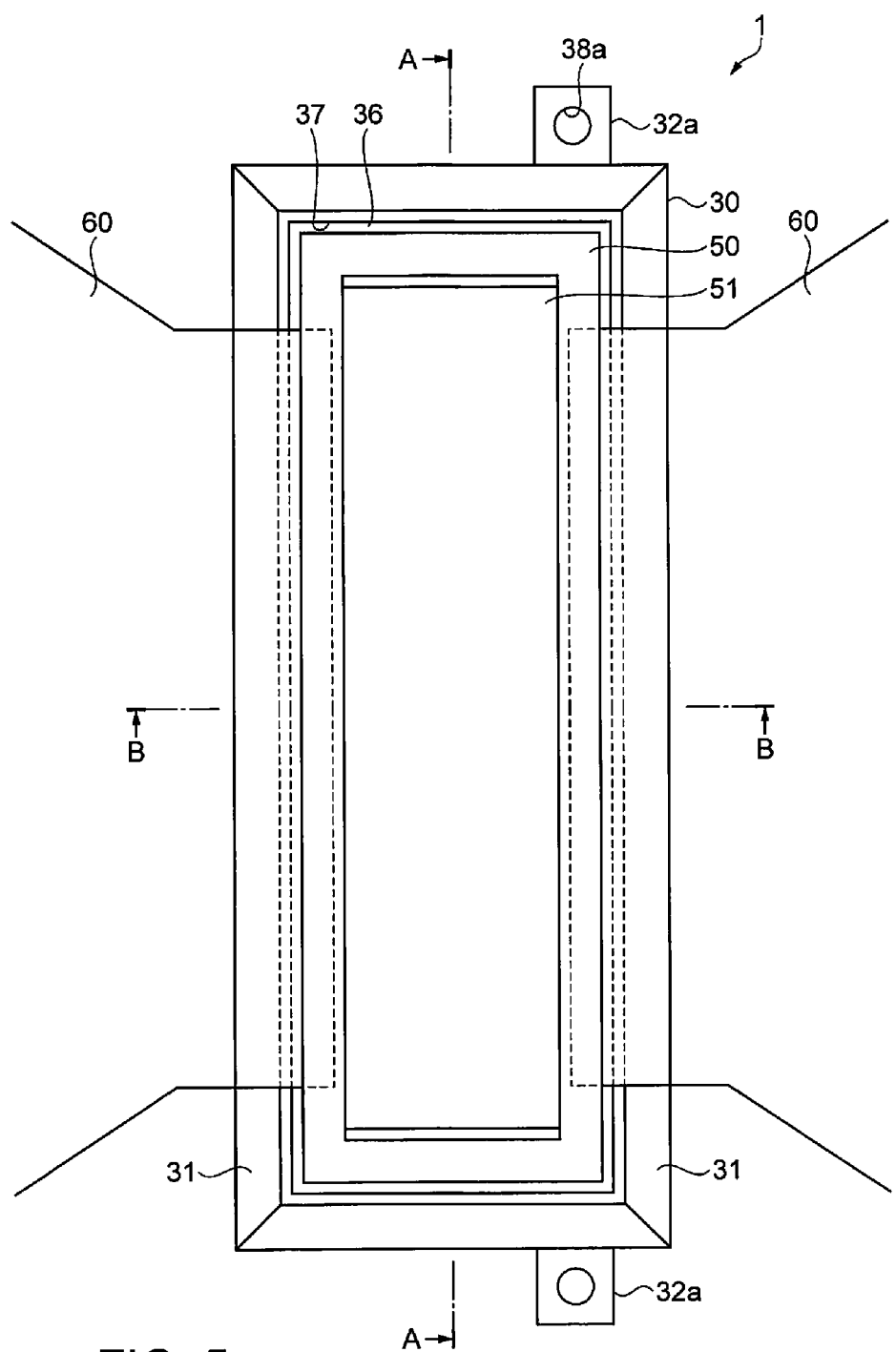
FIG. 5 is a plan view of an ultrasonic device according to the first embodiment.
Figure 6:
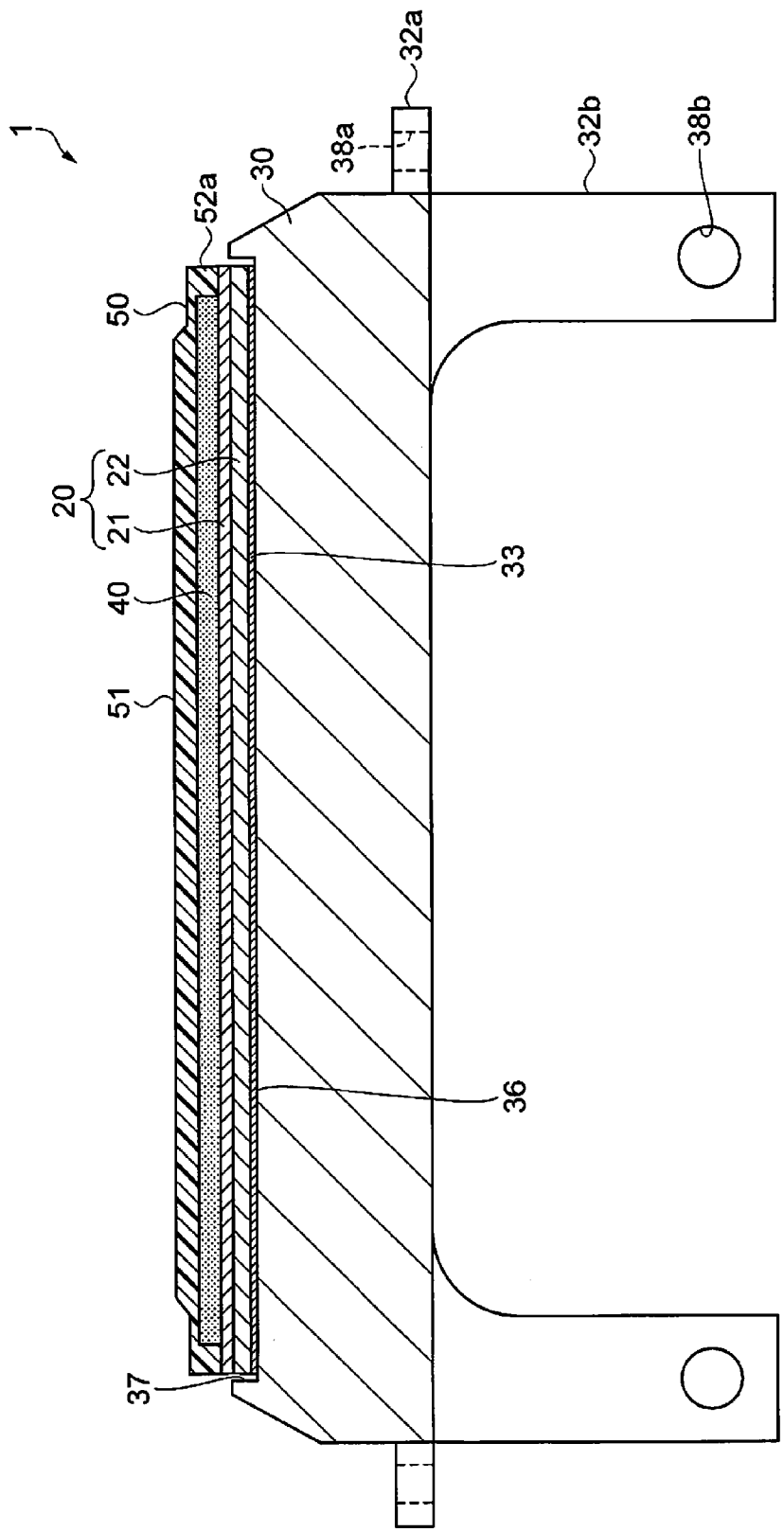
FIG. 6 is a sectional view of the ultrasonic device according to the first embodiment.
Figure 7:
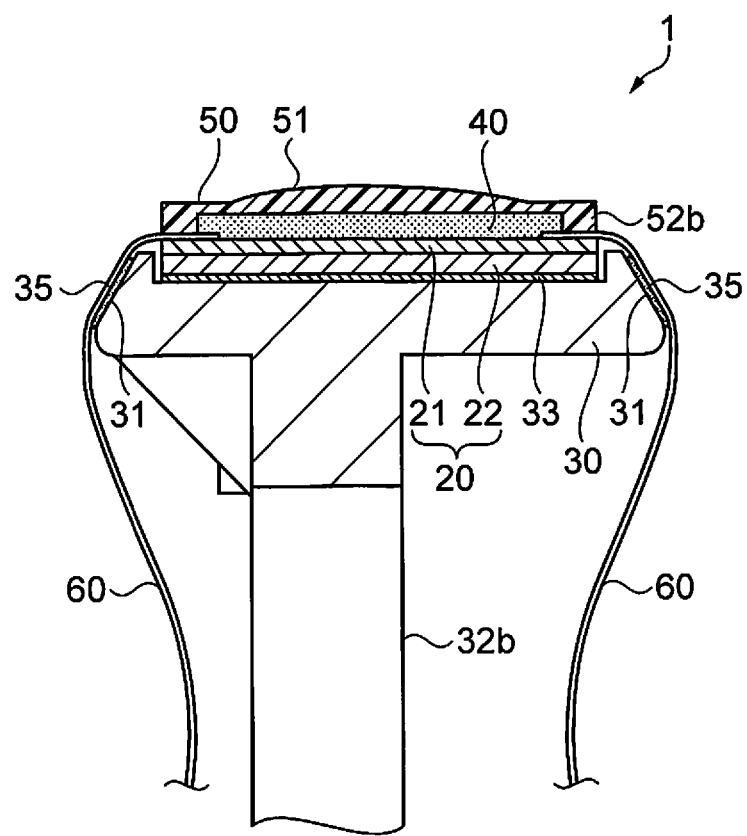
FIG. 7 is a sectional view of the ultrasonic device according to the first embodiment.

FIG. 5 is a plan view showing the configuration of the ultrasonic device, which corresponds to a view, as viewed in the direction of the arrow H in FIG. 3, of the ultrasonic probe. FIG. 6 is a sectional view taken along the broken line A-A of FIG. 5. FIG. 7 is a sectional view taken along the broken line B-B of FIG. 5.

As shown in FIGS. 5, 6, and 7, the ultrasonic device 1 includes an ultrasonic element array substrate 20, the support member 30, an acoustic matching layer 40, an acoustic lens 50, and the flexible printed circuit board (FPC) 60.

The ultrasonic element array substrate 20 has an element substrate 21 and a back plate 22.

The element substrate 21 is a substrate, having a rectangular shape in plan view, on which a plurality of ultrasonic elements are arranged in an array. This element substrate 21 is formed using a silicon substrate with a thickness of about 150 µm to 200 µm. The back plate 22, formed to have the same flat shape as the element substrate 21, is bonded to a surface, opposite to the surface formed with the elements, of the element substrate 21. The back plate 22 serves to suppress excessive vibration of the element substrate 21. A silicon substrate having a thickness of about 500 µm to 600 µm is used therefor. For this back plate 22, a metal plate may be used other than such a silicon substrate.

Depending on the circumstances, the ultrasonic device 1 may be formed without using the back plate 22.

The ultrasonic element array substrate 20 will be described later in detail.

The support member 30 is secured via an adhesive layer 33 to a surface (one surface), on which the ultrasonic elements are not formed, of the ultrasonic element array substrate 20, that is, the surface on the side of the back plate 22 in this embodiment. The adhesive layer 33 is formed of an adhesive, a double-sided adhesive tape, or the like.

The support member 30 has a flat portion 36 secured to the ultrasonic element array substrate 20. This flat portion 36 is formed at the bottom surface of a recess 37, and configured to facilitate the positioning of the ultrasonic element array substrate 20 (see FIG. 6). The support member 30 is formed of a metal or a resin such as an acrylic resin and an ABS resin.

In this way, the support member 30 is formed to have a larger area, in plan view in the thickness direction of the ultrasonic element array substrate 20, than the ultrasonic element array substrate 20, so that the ultrasonic element array substrate 20 avoids from abutting against other parts.

Further, the support member 30 is formed to have a sufficient thickness for supporting the flat portion 36. The support member 30 has a higher bending stiffness than the ultrasonic element array substrate 20.

The support member 30 includes an angled portion 31 provided along the outer edge of the surface to which the ultrasonic element array substrate 20 is secured. As shown in FIG. 5, the angled portion 31 is formed to have a periphery enlarging in a direction away from the ultrasonic element array substrate 20.

Further, the support member 30 has mounting portions 32a and 32b formed for mounting to the housing 132 of the ultrasonic probe 130 mentioned above. The mounting portions 32a and 32b respectively have through holes 38a and 38b, and are arranged so that the axis directions of mounting screws passing through the respective through holes 38a and 38b are orthogonal to each other (see FIG. 6). Therefore, the support member 30 can be fixed firmly to the housing 132 of the ultrasonic probe 130.

It should be noted that the shapes and arrangement of the mounting portions 32a and 32b can be appropriately designed, depending on the shape of the housing 132.

On a surface (the other surface), formed with the ultrasonic elements, of the ultrasonic element array substrate 20, a plurality of terminals (not shown in the figure) connected to the plurality of ultrasonic elements are exposed along the opposite long sides in plan view. These terminals are connected to the terminals of the FPC 60 (not shown in the figure), thus establishing electrical connection.

The FPC 60 is bonded to the angled portion 31 of the support member 30 by the adhesive member 35, such as an adhesive and a double-sided adhesive tape, so as to be secured thereto.

In this way, a part of the FPC 60 is secured to the support member 30. Therefore, when tension is applied to the FPC 60, the tension does not act on the connected portion to the ultrasonic element array substrate 20, which can prevent separation of the connected portion and damage to the ultrasonic element array substrate 20.

Further, the angled portion 31 is provided along the outer edge of the support member 30, and the FPC 60 is secured to the angled portion 31. Therefore, the FPC 60 extends along the angled portion 31 without being folded. Thus, it is possible to prevent the FPC 60 from folding, thereby preventing line disconnection.

The acoustic lens 50 having the same flat shape as the ultrasonic element array substrate 20 is arranged on a surface (the other surface), formed with the ultrasonic elements, of the ultrasonic element array substrate 20. The acoustic lens 50 is formed of a resin such as a silicone resin. It is possible to adjust the acoustic impedance by adding silica, or the like, to the silicone resin to change the specific gravity of the silicone resin.

The acoustic lens 50 is formed to have a lower bending stiffness than the ultrasonic element array substrate 20.

The acoustic matching layer 40 is formed between the ultrasonic element array substrate 20 and the acoustic lens 50. A silicone-based adhesive is used for the acoustic matching layer 40. Curing of the adhesive causes the ultrasonic element array substrate 20 and the acoustic lens 50 to be secured (adhered) to each other. The thus cured adhesive functions as the acoustic matching layer. In this way, the cured adhesive is filled between the ultrasonic element array substrate 20 and the acoustic lens 50 without gaps.

The acoustic lens 50 serves to guide ultrasound transmitted by the ultrasonic elements of the ultrasonic element array substrate 20 efficiently to a target object, and also guide echo waves reflected back from the object efficiently to the ultrasonic elements.

The acoustic matching layer 40 serves to relax the acoustic impedance mismatch between the acoustic lens 50 and the ultrasonic elements. That is, the acoustic matching layer 40 is adjusted to have an intermediate acoustic impedance between those of the ultrasonic element array substrate 20 and the acoustic lens 50.

Here, FIG. 8 shows a configuration of the acoustic lens 50. FIG. 8A is a top plan view of the acoustic lens 50. FIG. 8B is a plan view of the back side thereof. FIG. 8C is a partial sectional view taken along the broken line C-C of FIG. 8A. FIG. 8D is a partial sectional view taken along the broken line D-D of FIG. 8A.

The acoustic lens 50 has one surface provided with a lens portion 51 that is convex with a specific curvature in the thickness direction, and the opposite surface provided with projections 52 each having a protruding shape.

Figure 8A:
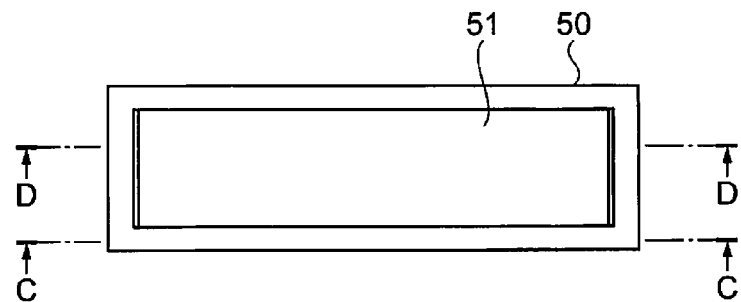
FIGS. 8A to 8D are explanatory diagrams illustrating a configuration of an acoustic lens of the ultrasonic device according to the first embodiment.
Figure 8B:
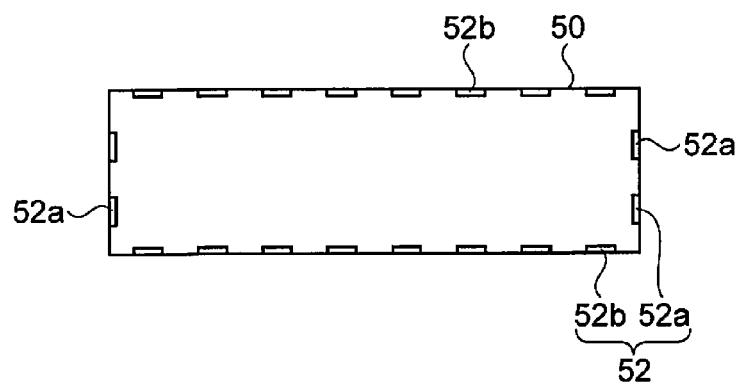

As shown in FIG. 8B, the projections 52 formed on the back side of the acoustic lens 50 include first projections 52a provided in the peripheral portion on the short sides of the acoustic lens 50, and second projections 52b provided in the peripheral portion on the long sides thereof.

Figure 8C:
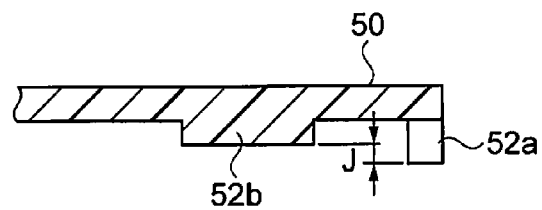

As shown in FIG. 8C, the first projections 52a and the second projections 52b arise from a base with the same thickness, and are configured so that the projection length is different therebetween. In this description, the first projections 52a each have a projection length larger than the second projections 52b. The dimension J, which is the difference in the projection length, is equal to the thickness of the FPC 60.

Figure 8D:
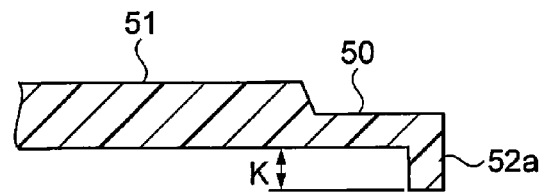

As shown in FIG. 8D, the dimension K, which is the length of the first projections 52a from the base, is set to be equal to the thickness of the acoustic matching layer 40.

It should be noted that the thickness of the acoustic matching layer 40 corresponds to the wavelength λ of the ultrasound to be used. The thickness, for example, is set to ¼λ.

Returning to FIG. 5 to FIG. 7, the first projections 52a are in contact with the surface of the ultrasonic element array substrate 20 (see FIG. 6), and the second projections 52b are in contact with the FPC 60 (see FIG. 7), in the state where the acoustic lens 50 is secured to the ultrasonic element array substrate 20.

In this way, the FPC 60 is pressed by the second projections 52b, so that the FPC 60 is prevented from being lifted in the connected portion between the ultrasonic element array substrate 20 and the FPC 60.

Further, the distance between the surface of the ultrasonic element array substrate 20 and the lens portion 51 can be set easily by setting the length dimension of the first projections 52a, so that the thickness of the acoustic matching layer 40 formed therebetween can be accurately set.

Furthermore, the first projections 52a and the second projections 52b are provided in the peripheral portion of the acoustic lens 50, and the FPC 60 is connected to the ultrasonic element array substrate 20 at a position inside the periphery of the acoustic lens 50. Therefore, the acoustic lens 50 can be stably mounted on the ultrasonic element array substrate 20. Further, excess adhesive forming the acoustic matching layer 40 is allowed to flow out through the gaps between the first projections 52a and the second projections 52b, thereby preventing air bubbles from remaining within the acoustic matching layer 40.

Moreover, since the FPC 60 is connected to the ultrasonic element array substrate 20 at a position inside the periphery of the acoustic lens 50, the connected portion is not exposed, and the connected portion can be protected by the acoustic matching layer 40.

As described above, the ultrasonic device 1 includes the support member 30 secured to one surface of the ultrasonic element array substrate 20 and the acoustic lens 50 secured to the other surface thereof. Further, the support member 30 is formed to have a larger area and a higher bending stiffness than the ultrasonic element array substrate 20, and the acoustic lens 50 is formed to have a lower bending stiffness than the ultrasonic element array substrate 20.

In this way, the ultrasonic element array substrate 20 has a structure of being secured with the support member 30 having a bending stiffness higher than the ultrasonic element array substrate 20. Therefore, the ultrasonic element array substrate 20 is reinforced, so that damage due to external forces can be prevented.

Further, the acoustic matching layer 40 is provided between the ultrasonic element array substrate 20 and the acoustic lens 50. Therefore, the acoustic lens 50 with a lower bending stiffness and the acoustic matching layer absorb external forces, which brings about an effect of relaxing the external forces applied to the ultrasonic element array substrate 20.

Furthermore, the ultrasonic device 1 integrally includes the ultrasonic element array substrate 20, the support member 30, the acoustic lens 50, and the acoustic matching layer 40. Therefore, when replacement of the ultrasonic element array substrate 20 is required, the ultrasonic device 1 only needs to be replaced. Thus, replacement is easy.

(3) Ultrasonic Elements and Ultrasonic Element Array Substrate

Next, the ultrasonic elements and the ultrasonic element array substrate (element substrate) of this embodiment are described.

Figure 9:
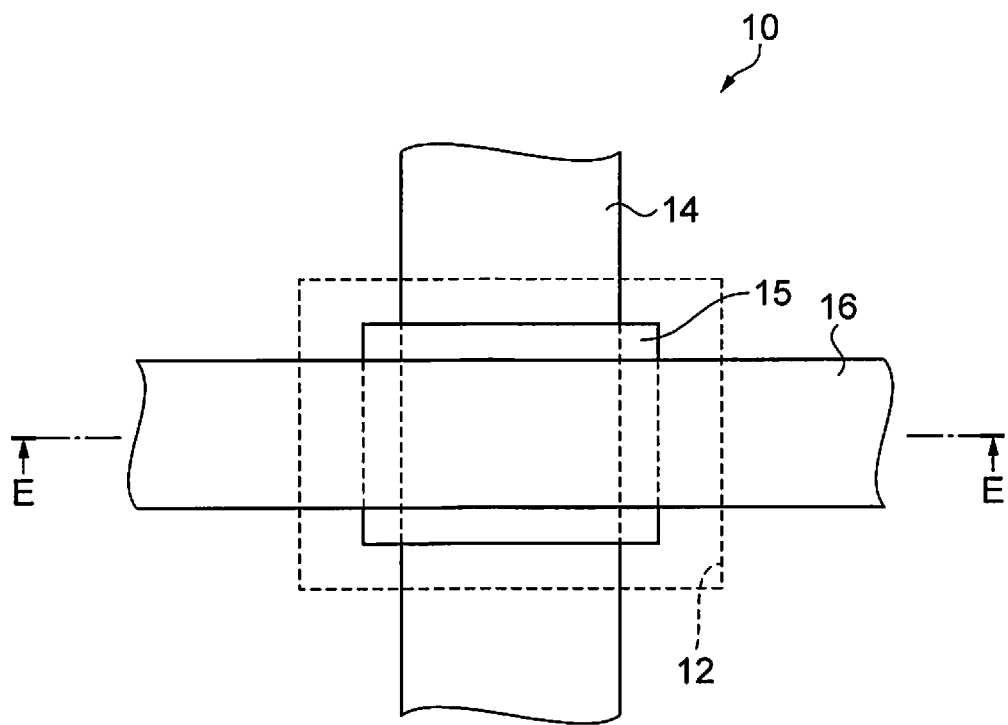
FIG. 9 is a plan view showing a schematic configuration of an ultrasonic element according to the first embodiment.
Figure 10:
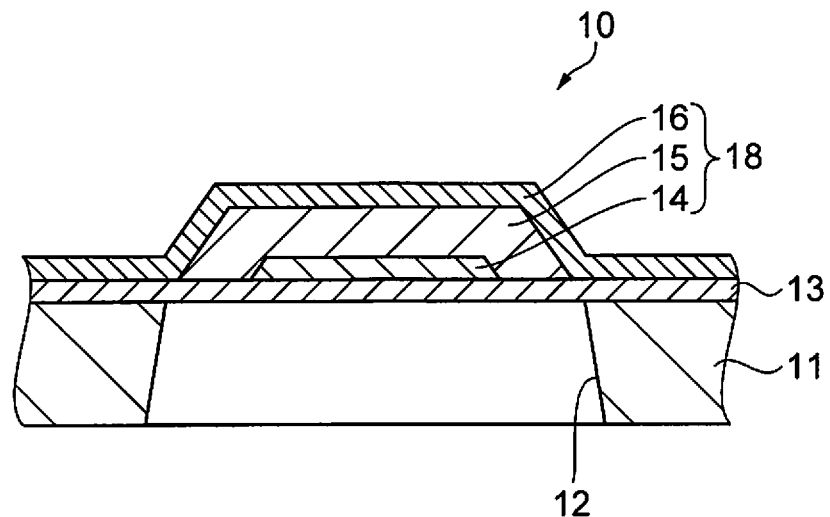
FIG. 10 is a sectional view showing the schematic configuration of the ultrasonic element according to the first embodiment.
Figure 11:
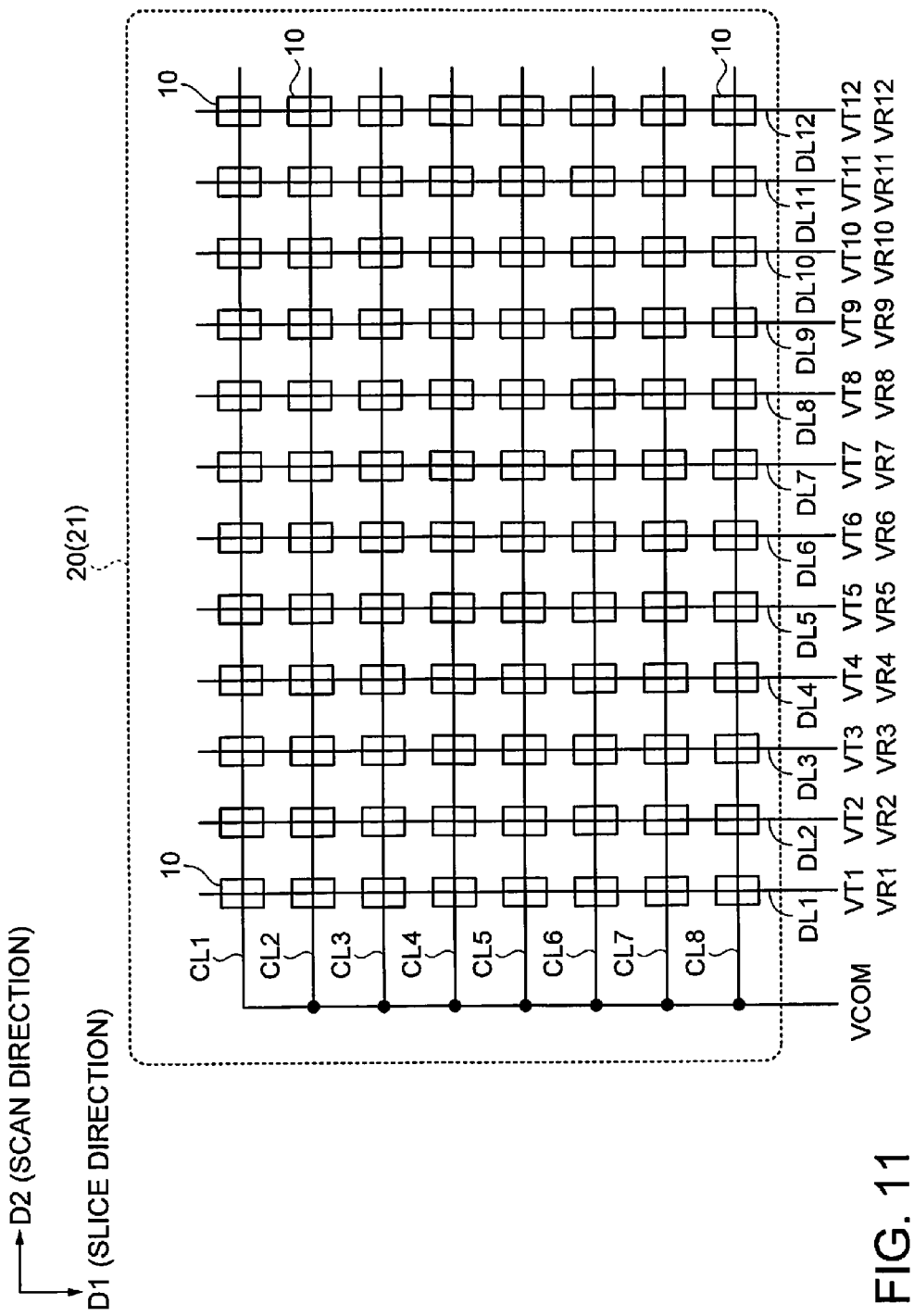
FIG. 11 is a conceptual diagram illustrating a schematic configuration of an ultrasonic element array substrate according to the first embodiment.

FIG. 9 is a schematic plan view of the ultrasonic elements of this embodiment. FIG. 10 is a schematic sectional view showing a cross section taken along the broken line E-E of FIG. 9. FIG. 11 is an explanatory diagram illustrating a schematic configuration of the ultrasonic element array substrate 20 of this embodiment.

As shown in FIG. 9 and FIG. 10, each ultrasonic element 10 has a base substrate 11, a vibrating membrane (membrane) 13 formed on the base substrate 11, and a piezoelectric body 18 provided on the vibrating membrane 13. The piezoelectric body 18 has a first electrode 14, a piezoelectric layer 15, and a second electrode 16.

The ultrasonic element 10 has an opening 12 in the base substrate 11 such as silicon, and includes the vibrating membrane 13 that covers and closes the opening 12.

The opening 12 is formed by subjecting the back side (surface on which the elements are not to be formed) of the base substrate 11 to etching such as reactive ion etching (RIE).

The vibrating membrane 13 has a double layer structure, for example, of a $SiO_2$ layer and a $ZrO_2$ layer. In the case where the base substrate 11 is a Si substrate, the $SiO_2$ layer can be formed by subjecting the surface of the substrate to thermal oxidation treatment. Further, the $ZrO_2$ layer can be formed on the $SiO_2$ layer by a technique such as sputtering. In the case where PZT, for example, is used as the piezoelectric layer 15, which will be described later, the $ZrO_2$ layer serves to prevent Pb that constitutes the PZT from diffusing into the $SiO_2$ layer. Further, the $ZrO_2$ layer also has an effect of improving the warpage efficiency corresponding to distortion of the piezoelectric layer.

The first electrode 14 is formed on the vibrating membrane 13. The piezoelectric layer 15 is formed on the first electrode 14. The second electrode 16 is further formed on the piezoelectric layer 15.

That is, the piezoelectric body 18 has a structure in which the piezoelectric layer 15 is interposed between the first electrode 14 and the second electrode 16.

The first electrode 14 is formed of a metal thin film. In the case where a plurality of ultrasonic elements are provided, the first electrode 14 may be wired so as to be extended to the outside of the element-formed region and connected to an adjacent ultrasonic element, as shown in FIG. 9.

The piezoelectric layer 15, for example, is formed of a PZT (lead zirconate titanate) thin film, and is provided to cover at least part of the first electrode 14. It should be noted that the material for the piezoelectric layer 15 is not limited to PZT. For example, lead titanate ($PbTiO_3$), lead zirconate ($PbZrO_3$), lead lanthanum titanate ($(Pb, La)TiO_3$), or the like, may be used therefor.

The second electrode 16 is formed of a metal thin film, and is provided to cover at least part of the piezoelectric layer 15. In the case where a plurality of ultrasonic elements are provided, the second electrode 16 may be wired so as to be extended to the outside of the element-formed region and connected to an adjacent ultrasonic element, as shown in FIG. 9.

The piezoelectric layer 15 expands and contracts in the in-plane direction by application of a voltage to the piezoelectric layer 15, that is, between the first electrode 14 and the second electrode 16. Accordingly, upon the application of a voltage to the piezoelectric layer 15, warpage that is convex on the opening 12 side occurs, which causes the vibrating membrane 13 to warp. Upon application of an AC voltage to the piezoelectric layer 15, the vibrating membrane 13 vibrates in the film thickness direction, and this vibration of the vibrating membrane 13 causes ultrasound to be emitted from the opening 12. The voltage (drive voltage) applied to the piezoelectric layer 15, for example, is 10 to 30 V peak to peak, and the frequency thereof is 1 to 10 MHz, for example.

The ultrasonic element 10 acts also as a receiving element to receive ultrasonic echo that is generated by reflection of the emitted ultrasound on the target object and returns back thereto. The ultrasonic echo vibrates the vibrating membrane 13, during which vibration causes a stress to be applied to the piezoelectric layer 15, resulting in generation of a voltage between the first electrode 14 and the second electrode 16. This voltage can be output as a reception signal.

An ultrasonic element array substrate including the aforementioned ultrasonic elements 10 arranged in an array is described below.

FIG. 11 shows a configuration of the ultrasonic element array substrate of this embodiment.

The ultrasonic element array substrate 20 includes a plurality of ultrasonic elements 10 arranged in an array, drive electrode lines DL, and common electrode lines CL.

The plurality of ultrasonic elements 10 are arranged into a matrix with m rows and n columns. In this embodiment, eight rows along a first direction D1 and twelve columns along a second direction D2 intersecting the first direction D1 are arranged.

The drive electrode lines DL1 to DL12 are each formed along the first direction D1.

During the transmission period in which ultrasound is emitted, the transmission signals VT1 to VT12 output by the aforementioned processing circuit 150 are supplied to the respective ultrasonic elements 10 via the drive electrode lines DL1 to DL12. Meanwhile, during the reception period in which ultrasonic echo signals are received, the reception signals VR1 to VR12 from the ultrasonic elements 10 are output to the processing circuit 150 via the drive electrode lines DL1 to DL12.

Common electrode lines CL1 to CL8 are each formed along the second direction D2.

The common electrode lines CL1 to CL8 are supplied with a common voltage VCOM. This common voltage only needs to be a constant direct current voltage, and is not necessarily 0 V, namely, a ground potential.

It should be noted that the arrangement of the ultrasonic elements 10 is not limited to the matrix arrangement with m rows and n columns shown in FIG. 11.

In the transmission period, a voltage that is the difference between the transmission signal voltage and the common voltage is applied to each of the ultrasonic elements 10, and ultrasound is emitted at a specific frequency.

As described above, the ultrasonic imaging apparatus and the ultrasonic probe of this embodiment each include the ultrasonic device 1 that prevents damage to the ultrasonic element array substrate 20, which allows the ultrasonic imaging apparatus 100 and the ultrasonic probe 130 with high reliability to be provided.

Figure 12:
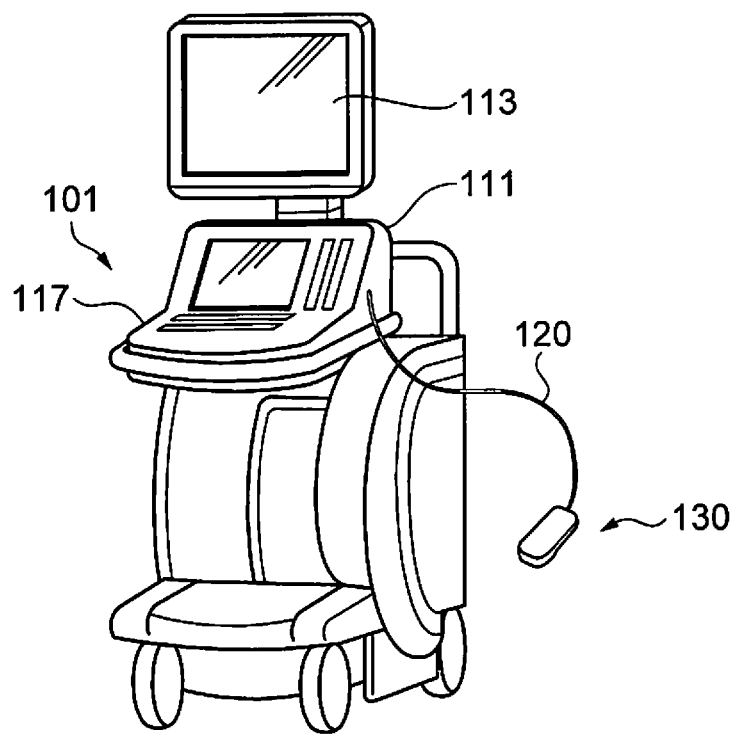
FIG. 12 is a schematic outline showing a configuration of another ultrasonic imaging apparatus.

Though a portable ultrasonic imaging apparatus is exemplified in the above-mentioned embodiment, FIG. 12 shows a specific configuration example of an ultrasonic imaging apparatus of another embodiment.

An ultrasonic imaging apparatus 101 is a stationary ultrasonic imaging apparatus, and includes the ultrasonic probe 130.

The ultrasonic imaging apparatus 101 has an apparatus body (electronic equipment body) 111, a display 113 that displays image data to be displayed, a user-interface unit (UI unit) 117, the ultrasonic probe 130, and the cable 120.

Effects of the invention can be exerted by employing such a stationary ultrasonic imaging apparatus.

Further, the ultrasonic imaging apparatus of this embodiment can be used for in-vivo measurements of fat thickness, muscle thickness, bloodstream, bone density, etc.

The invention is not limited to the foregoing embodiments. The specific arrangements and procedures in practicing the invention may be altered by another arrangement or the like, as necessary, as long as the advantages of the invention can be achieved. Many modifications can be made by a person of ordinary skill in the art without departing from the technical scope of the invention.

The entire disclosure of Japanese Patent Application No. 2013-012946, filed Jan. 28, 2013 is expressly incorporated by reference herein.

What is claimed is:

1. An ultrasonic device comprising:
an ultrasonic element array substrate having a plurality of ultrasonic elements that each include a piezoelectric body and perform at least one of transmission and reception of ultrasound;
an acoustic lens secured via an acoustic matching layer to a surface, formed with the ultrasonic elements, of the ultrasonic element array substrate, the acoustic lens having a lens portion that focuses the ultrasound; and
a support member secured to a surface, opposite to the surface formed with the ultrasonic elements, of the ultrasonic element array substrate, wherein
the support member is formed to have a larger area, in plan view in the thickness direction of the ultrasonic element array substrate, and a higher bending stiffness than the ultrasonic element array substrate, and
the acoustic lens is formed to have a lower bending stiffness than the ultrasonic element array substrate.

2. The ultrasonic device according to claim 1, further comprising:
an acoustic matching layer filled between the ultrasonic element array substrate and the acoustic lens, wherein
the acoustic matching layer is formed of a resin secured to the ultrasonic element array substrate and the acoustic lens.

3. The ultrasonic device according to claim 1, wherein
the acoustic lens has a plurality of first projections in contact with the ultrasonic element array substrate.

4. The ultrasonic device according to claim 3, wherein
the first projections are provided in a peripheral portion of the acoustic lens in the plan view.

5. An ultrasonic probe comprising:
the ultrasonic device according to claim 3; and
a housing supporting the ultrasonic device.

6. Electronic equipment comprising:
the ultrasonic device according to claim 3; and
a processing circuit that is connected to the ultrasonic device and processes an output of the ultrasonic device.

7. An ultrasonic imaging apparatus comprising:
the ultrasonic device according to claim 3;
a processing circuit that is connected to the ultrasonic device and processes an output of the ultrasonic device so as to generate an image; and
a display that displays the image.

8. The ultrasonic device according to claim 1, further comprising:
a flexible printed circuit board connected to the surface, formed with the ultrasonic elements, of the ultrasonic element array substrate, wherein
the flexible printed circuit board is electrically connected to the ultrasonic element array substrate, and
a part of the flexible printed circuit board is secured to the support member.

9. The ultrasonic device according to claim 8, wherein
the support member includes an angled portion provided at a part of its outer edge, and
the flexible printed circuit board is secured to the angled portion.

10. The ultrasonic device according to claim 8, wherein
the acoustic lens has a plurality of the second projections, in contact with the flexible printed circuit board, pressing the flexible printed circuit board against the ultrasonic element array substrate.

11. The ultrasonic device according to claim 10, wherein
the flexible printed circuit board is electrically connected with the ultrasonic element array substrate at a position between the second projections of the acoustic lens and the ultrasonic elements, in plan view in the thickness direction of the ultrasonic element array substrate.

12. An ultrasonic probe comprising:
the ultrasonic device according to claim 10; and
a housing supporting the ultrasonic device.

13. Electronic equipment comprising:
the ultrasonic device according to claim 10; and
a processing circuit that is connected to the ultrasonic device and processes an output of the ultrasonic device.

14. An ultrasonic probe comprising:
the ultrasonic device according to claim 8; and
a housing supporting the ultrasonic device.

15. Electronic equipment comprising:
the ultrasonic device according to claim 8; and
a processing circuit that is connected to the ultrasonic device and processes an output of the ultrasonic device.

16. An ultrasonic imaging apparatus comprising:
the ultrasonic device according to claim 8;
a processing circuit that is connected to the ultrasonic device and processes an output of the ultrasonic device so as to generate an image; and
a display that displays the image.

17. The ultrasonic device according to claim 1, wherein
the ultrasonic element array substrate includes:
a base substrate provided with a plurality of openings arranged in an array;
a vibrating membrane formed to cover the openings, the vibrating membrane being displaceable in the film thickness direction; and
a piezoelectric body provided on the vibrating membrane, and
the piezoelectric body includes:
a first electrode provided on the vibrating membrane;
a piezoelectric layer provided to cover at least part of the first electrode; and
a second electrode provided to cover at least part of the piezoelectric layer.

18. An ultrasonic probe comprising:
the ultrasonic device according to claim 1; and
a housing supporting the ultrasonic device.

19. Electronic equipment comprising:
the ultrasonic device according to claim 1; and
a processing circuit that is connected to the ultrasonic device and processes an output of the ultrasonic device.

20. An ultrasonic imaging apparatus comprising:
the ultrasonic device according to claim 1;
a processing circuit that is connected to the ultrasonic device and processes an output of the ultrasonic device so as to generate an image; and
a display that displays the image.

* * * * *